United States Patent
Chuang et al.

(10) Patent No.: US 11,719,643 B2
(45) Date of Patent: Aug. 8, 2023

(54) SYSTEM AND METHOD FOR DETECTION OF DUST MITE ANTIGENS

(71) Applicant: National Tsing Hua University, Hsinchu (TW)

(72) Inventors: Chun-Yu Chuang, Hsinchu County (TW); Pin-Hsuan Yeh, Hsinchu County (TW); Chao-Ming Tsen, Kaohsiung (TW); Ching-Wei Yu, Taipei (TW); Wei-Chung Chao, Hsinchu (TW); Yung-Hsiang Wang, New Taipei (TW); Cheng-Chien Li, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 1111 days.

(21) Appl. No.: 16/422,178

(22) Filed: May 24, 2019

(65) Prior Publication Data
US 2019/0360938 A1 Nov. 28, 2019

(30) Foreign Application Priority Data
May 24, 2018 (TW) ................................ 107117819

(51) Int. Cl.
*G01N 21/65* (2006.01)
*C12Q 1/37* (2006.01)
(Continued)

(52) U.S. Cl.
CPC ............. *G01N 21/658* (2013.01); *C12Q 1/37* (2013.01); *G01N 33/5308* (2013.01);
(Continued)

(58) Field of Classification Search
CPC ............... G01N 21/658; G01N 21/553; G01N 33/54373; G01N 2333/96413;
(Continued)

(56) References Cited

U.S. PATENT DOCUMENTS 7,192,703 B2    3/2007  Sun et al.
2011/0116089 A1*  5/2011  Schmidt ............... G01N 21/658
                                                        356/244

FOREIGN PATENT DOCUMENTS

TW             M523295 U      6/2016
WO     WO-2013065016 A1 *    5/2013 ........... C12N 15/115

OTHER PUBLICATIONS

Gartia et al ("Rigorous surface enhanced Raman spectral characterization of large-area high-uniformity silver-coted tapered silica nanopillar arrays", Nanotechnology, 21 (2010), 395701, p. 1-9) (Year: 2010).*

(Continued)

*Primary Examiner* — Christopher L Chin
(74) *Attorney, Agent, or Firm* — Muncy, Geissler, Olds & Lowe, P.C.

(57) ABSTRACT

A method for detecting dust mite antigens includes the steps of collecting a dust sample, applying an extraction and cleanup procedure for dust mite antigens from the dust sample in order to obtain a sample solution ready for measurement, and placing the sample solution on a SERS chip without immunological modification and under a Raman spectrometer for SERS detection in order to identify whether any dust mite antigens exist in the sample solution.

3 Claims, 12 Drawing Sheets

(51) Int. Cl.
*G01N 33/543* (2006.01)
*G01N 33/53* (2006.01)

(52) U.S. Cl.
CPC .............. *G01N 33/54373* (2013.01); *G01N 2333/43582* (2013.01); *G01N 2333/96413* (2013.01)

(58) Field of Classification Search
CPC ..... G01N 2333/43582; G01N 2800/24; G01N 33/5308; C12Q 1/37
USPC ............... 356/301, 952; 422/82.05, 82.11; 435/288.7; 436/164, 524, 525, 805
See application file for complete search history.

(56) References Cited

OTHER PUBLICATIONS

Shen et al ("Electrochemical aptasensor for detecting Der p2 allergen using polycarbonate-based double-generation gold nanoparticle chip", Sensing and Bio-Sensing Research 13 (2017), 75-80 (Year: 2017).*

* cited by examiner

SYSTEM AND METHOD FOR DETECTION OF DUST MITE ANTIGENS

BACKGROUND OF INVENTION

1. Field of Invention

The present invention relates to a system and method for detecting dust mite antigens and, more particularly, to a non-immune system and method for detecting dust mite antigens.

2. Related Prior Art

Dust mite is one of the common biological allergens in indoor dust. Both of the European *Dermatophagoides pteronyssinus* (Der p) and the American *Dermatophagoides farina* (Der f) are the most common species of dust mites to affect human health. Previous studies have revealed that *Dermatophagoides pteronyssinus* group 1 allergen (Der p 1) carrying cysteine proteases can initiate a specifically allergic immune response in children to attack asthma when they are exposed to dust mites. Now, Der p 1 in indoor dust has been used to be an index for assessing the probability and the risk of asthma occurrence. In general, inhalation of Der p1 at 2 ppm could induce asthma. Moreover, another type of dust mite found often in indoor dust is *Dermatophagoides farinae* group 1 allergen (Der f 1) also carrying cysteine proteases. If the subjects are allergic to dust mites via inhaling dust corpses or excrement, the allergen also called antigen contained in the dust mites are detectable in their blood. When human T helper cells detect foreign substances, they deliver messages to B cells to produce immunoglobulin E (IgE) that bonds with mast cells, antigens and eosinophiles to release chemical substances such as histamine, and cause an inflammatory response. The entire process is called immediate hypersensitivity. Nonetheless, there has not been any effective and rapid methods for detecting mite antigens in the dust till now.

A conventional method for detecting dust mite antigens is enzyme-linked immunosorbent assay (ELISA). The ELISA assay uses the specificity of the binding of an antigen with an enzyme-linked antibody, and the subsequent reaction with an added enzyme substrate produces a detectable color or fluorescent signal. Antigens that are bonded with a solid carrier such as a plastic aperture plate still possess immune activity. Hence, with the bonding mechanism in addition to the enzyme coloring, it can be shown whether certain antigens or antibodies exist. The shade of the color can be used for a quantitative analysis. However, there are problems with the search for highly specific and active antibodies because there are many variables in the production of the antibodies. Furthermore, using immune response to detect dust mite antigens in the environment is complicated and time-consuming, not suitable for rapid screening. In fact, due to procedural differences between collecting household dust to testing at an inspection center, the current method is unable to meet the needs of household inspection.

Currently, Raman technology has been applied to biomolecular detection but is mostly used in the immune reaction assay which bonds antibodies with antigens for detection and analysis. U.S. Pat. No. 7,192,703 discloses a "biomolecule analysis by rolling circle amplification and SERS detection" to increase the quality of detection signals. This conventional method combines rolling circle amplification (RCA) with immune reaction to enhance Raman signals. However, it should be noted that this conventional method needs to work with antibodies, primers, enzymes and probes marked with fluorescence, and is hence complicated. Moreover, at present, the biomolecules of test objects have not yet been detected for dust mite antigens.

Taiwanese Patent No. M523295 discloses an apparatus for catching dust mites. This apparatus traps actively dust mites in the environment, and thereby reduces the production of allergens. This conventional apparatus further provides a test kit for detecting the result of trapping so that the efficiency of trapping mites can be observed by the naked eyes directly. In detail, after the trapping is completed, the color reagent is uniformly coated on a capture layer of the trapping apparatus, and then sandwiched it into a transparent substrate. The color reagent is heated at 50° C. to 70° C. for 10 minutes or laid at room temperature for 3 to 10 days. The trapped dust mites, if any, will be dyed, and the trapping efficiency can be observed with bare eyes. However, this method is merely used to evaluate roughly the amount of the dust mites in the environment, not calculate precisely.

The present invention is therefore intended to obviate or at least alleviate the problems encountered in prior art.

SUMMARY OF INVENTION

It is an objective of the present invention to provide an effective and efficient method for detecting dust mite antigens.

To achieve the foregoing objective, the method includes the steps of (a) collecting a dust sample, (b) extracting dust mite antigens from the dust sample and cleaning up the dust mite antigens, thereby providing a to-be-examined sample, and (c) placing the testing sample on a SERS chip without immunological modification, and using a Raman spectrometer to impose surface-enhanced Raman examination on the to-be-examined sample placed on the SERS chip, thereby determining whether certain dust mite antigens exist in the dust sample.

In another aspect, the Raman spectrometer builds the spectrum database at least for one standard dust mite antigen. The information of the database includes Raman spectrums and corresponding standard curves for the relationship between the characteristic peak signals and the concentrations. In the Raman determination, the Raman spectrum of the to-be-examined sample is referred with the Raman spectrum of the standard dust mite antigen to determine whether any dust mite antigen identical to the standard dust mite antigen exists in the to-be-examined sample, and the standard curve is used to calculate the concentration of the dust mite antigens in the to-be-examined sample if there is dust mite antigens determined identically to the standard dust mite antigen in the to-be-examined sample.

In another aspect, the step of (b) extracting dust mite antigens includes the step of using TBE extract buffer to extract dust mite antigens from the dust sample, and the TBE extract buffer includes tris borate buffer, bicarbonate, phosphate and NaCl.

In another aspect, v

In another aspect, the at least one standard dust mite antigen includes a standard dust mite allergen Der p1 or a standard dust mite allergen Der f1.

It is another objective of the present invention to provide a system for detecting dust mite antigen according to the above-mentioned method.

To achieve the foregoing objective, the system includes a SERS chip and Raman spectrometer. The SERS chip is not subjected to immunological modification and used to carry one to-be-examined sample. The Raman spectrometer is used to impose a surface-enhanced Raman determination on the dust sample on the SERS chip, wherein the Raman spectrometer builds the spectrum database at least for one standard dust mite antigen. The information of the database includes Raman spectrums and corresponding standard curves for the relationship between the characteristic peak signals and the concentrations. In the Raman determination, the Raman spectrum of the to-be-examined sample is referred with the Raman spectrum of the standard dust mite antigen to determine whether any dust mite antigen identical to the standard dust mite antigen exists in the to-be-examined sample, and the standard curve is used to calculate the concentration of the dust mite antigens in the to-be-examined sample if there is dust mite antigens determined identically to the standard dust mite antigen in the to-be-examined sample.

In another aspect, the nanogold coated on an array structure of silver columns extending from a surface.

Other objectives, advantages and features of the present invention will be apparent from the following description referring to the attached drawings.

BRIEF DESCRIPTION OF DRAWINGS

The present invention will be described via detailed illustration of the preferred embodiment referring to the drawings wherein.

DETAILED DESCRIPTION OF PREFERRED EMBODIMENT

Figure 1:
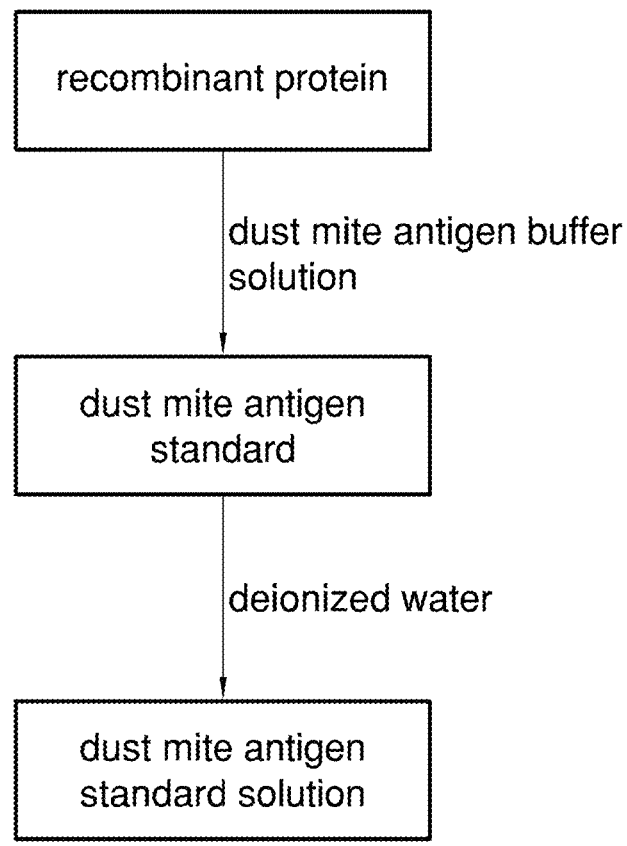
FIG. 1 is a flow chart of a process for producing the standard solution of dust mite antigens according to the preferred embodiment of the present invention.
Figure 2A:
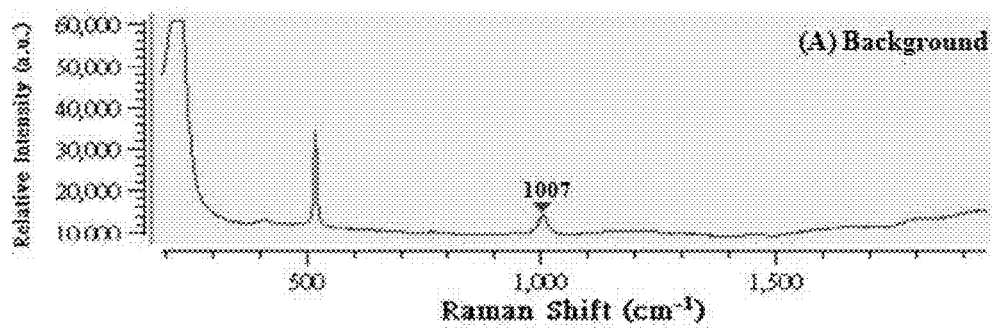
FIGS. 2A to 2H are Raman spectrums of the standard solution of dust mite antigen Der f1 with different concentrations.
Figure 2B:
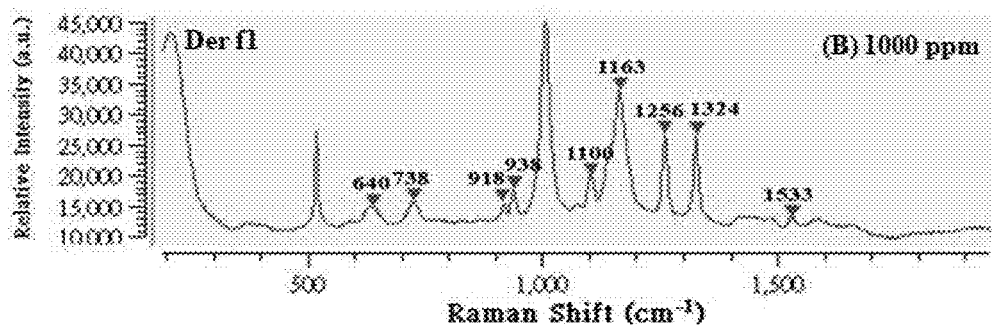
Figure 2C:
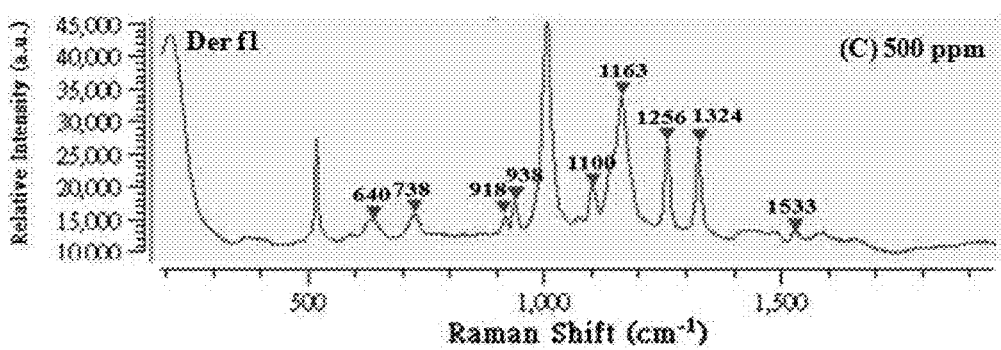
Figure 2D:
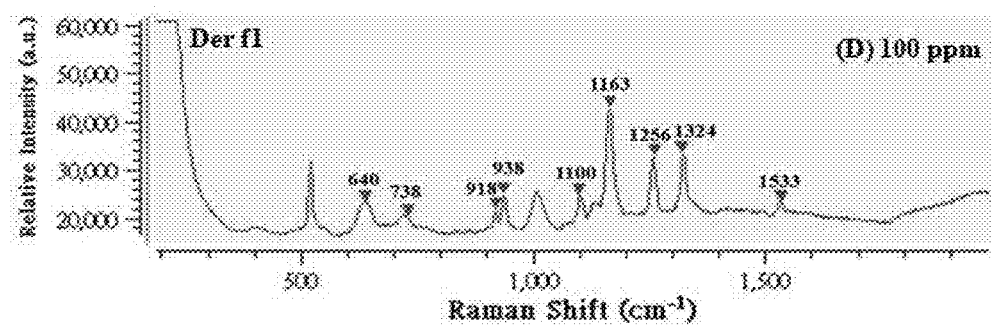
Figure 2E:
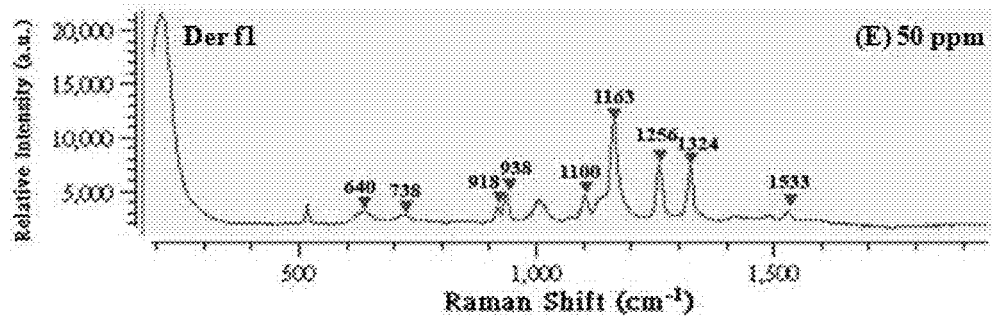
Figure 2F:
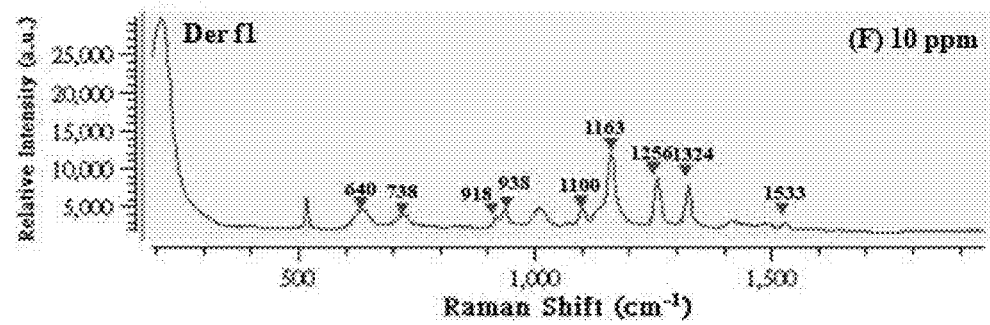
Figure 2G:
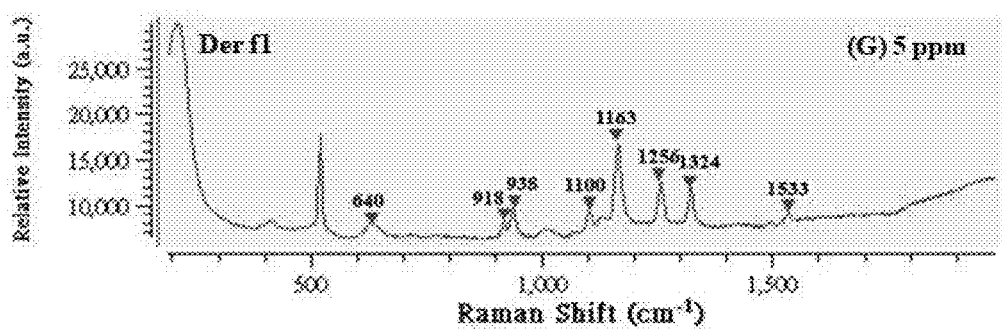
Figure 2H:
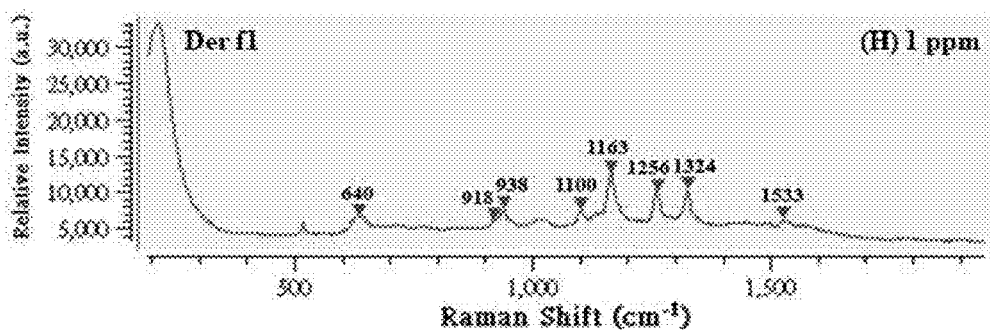
Figure 3A:
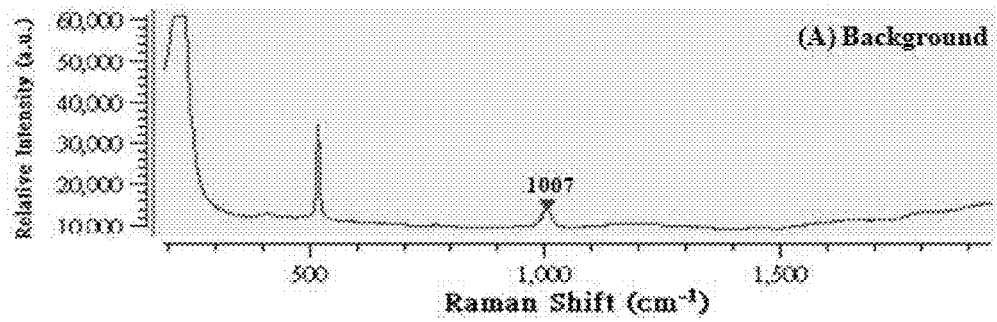
FIGS. 3A to 3H are Raman spectrums of the standard solution of dust mite antigen Der p1 with different concentrations.
Figure 3B:
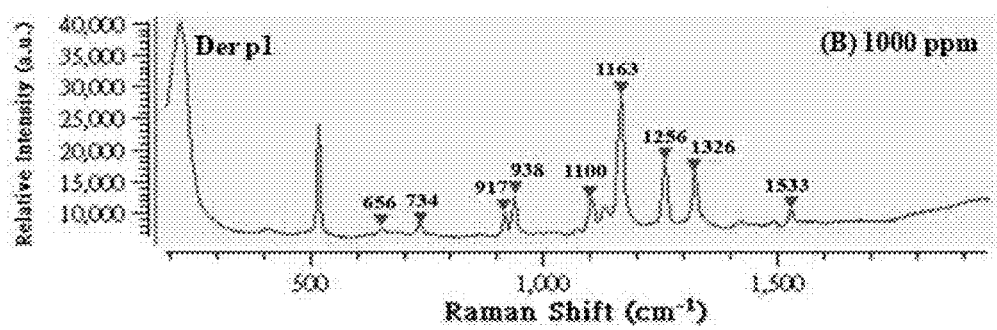
Figure 3C:
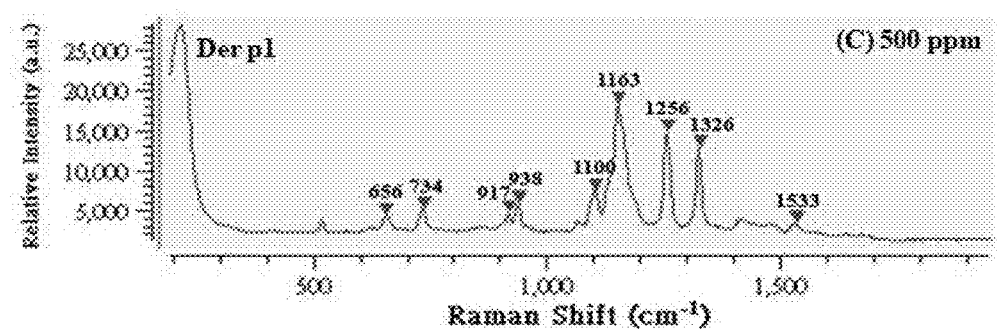
Figure 3D:
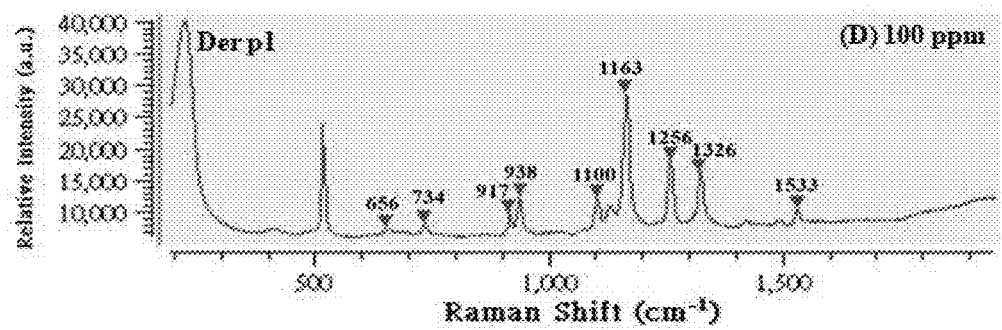
Figure 3E:
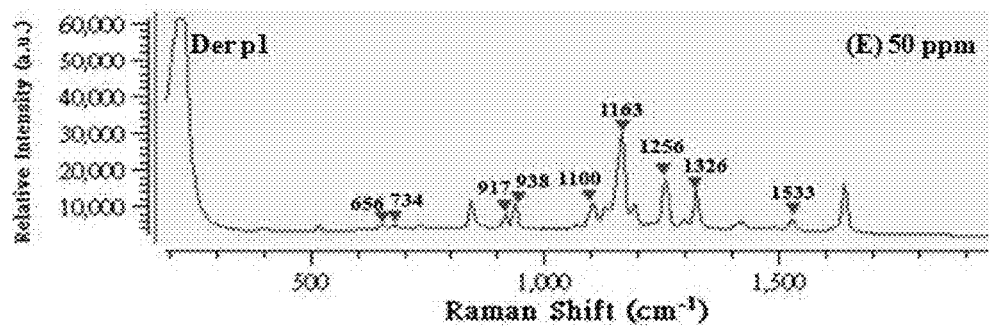
Figure 3F:
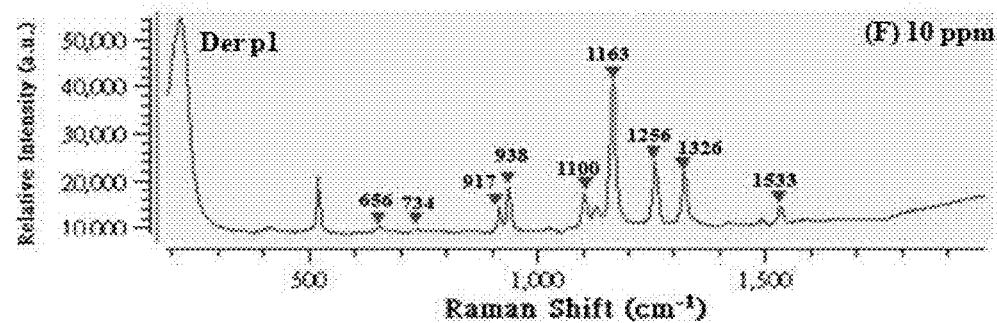
Figure 3G:
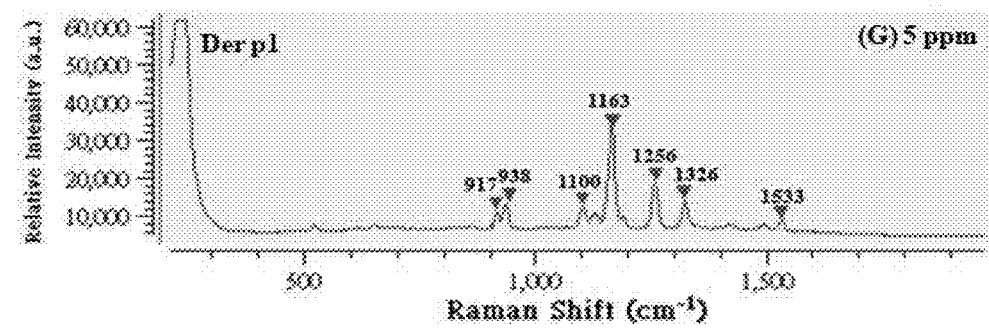
Figure 3H:
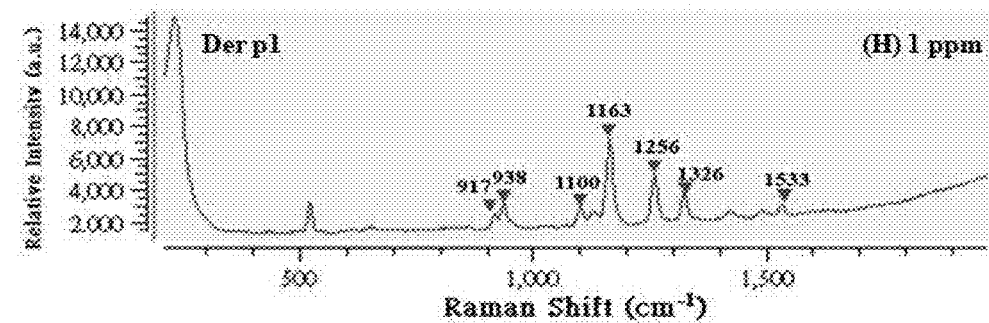

In a method for detecting dust mite antigens according to the preferred embodiment of the present invention, at first, (a) a dust sample is collected, then, (b) dust mite antigens are extracted from the dust sample and cleaned up, and thereby (c) providing a to-be-examined sample. Then, the to-be-examined sample is laid on a SERS chip without immunological modification, and a Raman spectrometer is used to impose SERS examination on the to-be-examined sample on the SERS chip to determine whether any certain dust mite antigens exist in the to-be-examined sample. It should be noted that the dust sample can be added with TBE extract buffer during the extraction of the to-be-examined sample from the dust sample to facilitate the determination of the to-be-examined sample.

In detail, t the Raman spectrometer builds the spectrum database at least for one standard dust mite antigen. The information of the database includes Raman spectrums and corresponding standard curves for the relationship between the characteristic peak signals and the concentrations. In the Raman determination, the Raman spectrum of the to-be-examined sample is referred with the Raman spectrum of the standard dust mite antigen to determine whether any dust mite antigen identical to the standard dust mite antigen exists in the to-be-examined sample, and the standard curve is used to calculate the concentration of the dust mite antigens in the to-be-examined sample if there is dust mite antigens determined identically to the standard dust mite antigen in the to-be-examined sample. Preferably, nanogold is coated on an array structure of silver columns extending from a surface of the SERS chip.

There is provided a system for detecting dust mite antigens according to the above-mentioned method. The system includes a SERS chip and a Raman spectrometer. The SERS chip is not subjected to immunological modification. The SERS chip is used to carry a to-be-examined sample. The Raman spectrometer is used to execute surface-enhanced Raman examination of the to-be-examined sample on the SERS chip. Preferably, the Raman spectrometer builds the spectrum database at least for one standard dust mite antigen. The information of the database includes Raman spectrums and corresponding standard curves for the relationship between the characteristic peak signals and the concentrations. In the Raman determination, the Raman spectrum of the to-be-examined sample is referred with the Raman spectrum of the standard dust mite antigen to determine whether any dust mite antigen identical to the standard dust mite antigen exists in the to-be-examined sample, and the standard curve is used to calculate the concentration of the dust mite antigens in the to-be-examined sample if there is dust mite antigens determined identically to the standard dust mite antigen in the to-be-examined sample.

In the preferred embodiment, standards of two common dust mite antigens Der p1 and Der f1 are used for the SERS determination and analysis to build the surface-enhanced Raman spectrum dataset and the standard curves for the relationship between the characteristic peak signals and the concentrations. The concentrations of samples of the standard dust mite antigen are 1, 5, 10, 50, 100, 500 and 1000 ppm. In addition, cotton wool is used to simulate dust matrix and added with the standard dust mite antigen as an internal label. After preprocessing, i.e., using buffer solution and cleanup columns to soak and extract, the samples are dropped on the SERS chip without immunological modification, and the detection of the dust mite antigens can be executed and completed in 10 seconds.

The Raman spectrometer is preferably Wasatch Photonics 785 L, with laser wavelength of 785 nm and a wave number of 350 to 2000 $cm^{-1}$. The SERS chip used in the Raman spectrum determination includes nanogold coated on an array structure of silver columns extending from a surface of a glass film substrate made by glancing deposition. The thickness of the SERS chip is about 289±5 nm. The SERS examination is executed in the Raman system with a power of 100 mW, magnification of lens 4×, integration time of 500 ms, spectrums overlapped for 16 times. Time for observation and recording is 15 seconds to 2 minutes.

The process for detecting dust mite antigens, and its results will be described.

Firstly, dust mite antigen standard solutions are produced. Referring to FIG. 1, to produce the standard solutions of dust mite antigen, the amount of Der f1 recombinant protein (or Der p1 recombinant protein) is dissolved in dust mite antigen buffer solution, thereby providing a dust mite antigen standard. Then, the dust mite antigen standard is diluted by deionized water, thereby the standard solutions of dust mite antigen at different concentrations are prepared. Preferably, the Der f1 recombinant protein is ALR-004 provided by ProSpec, New Brunswick, N.J., and the Der p1 recombinant protein is ALR-003 provided by the same company. The dust mite antigen buffer solution is mixture of 60 mM NaCl, 50 mM Tris-HCl, pH 8.0 and 1.2 M Urea with one another. To produce the standard solution of dust mite antigen, the Der f1 recombinant protein (or Der p1 recombinant protein) is dissolved in the dust mite antigen buffer solution and diluted by deionized water to provide dust mite antigen standard solutions at 1 ppm, 5 ppm, 10 ppm, 50 ppm, 100 ppm, 500 ppm and 1000 ppm for example.

Figure 4:
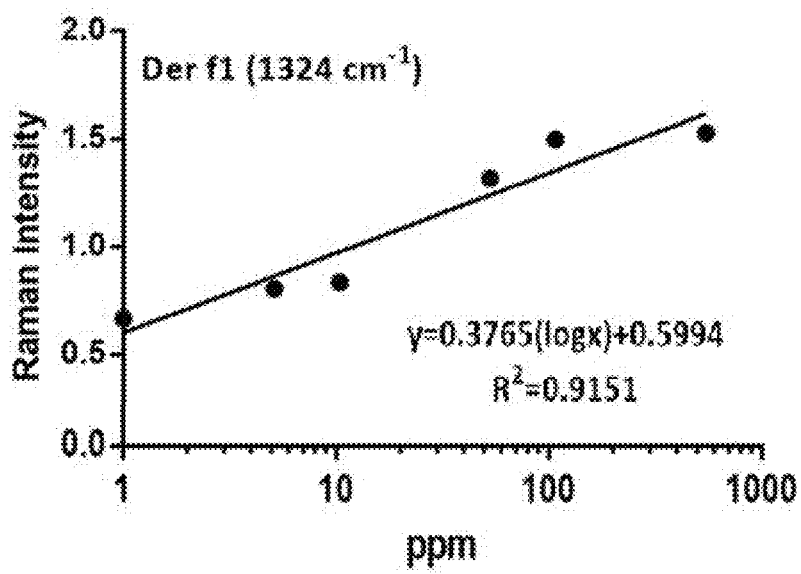
FIG. 4 shows the correlation between the concentrations of the standard solutions of dust mite antigen Der f1 and the intensity of Raman signals.
Figure 5:
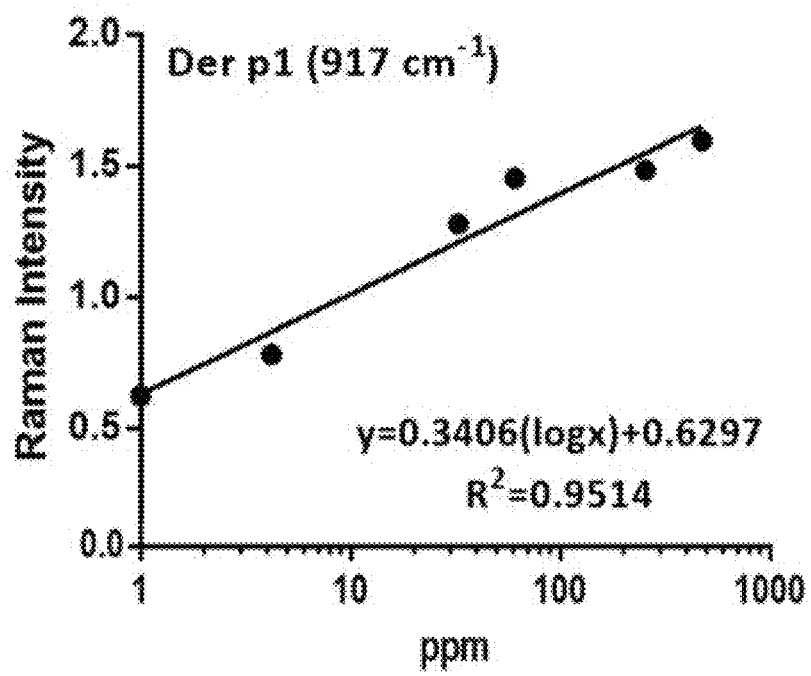
FIG. 5 shows the correlation between the concentrations of the standard solutions of dust mite antigen Der p1 and the intensity of Raman signals.

After the production of the standard solutions of dust mite antigen is completed, 3 µl of dust mite antigen buffer solution is dropped on the SERS chip, and subjected to the SERS examination so that it can be used as a background value. Then, 3 µl of each of the dust mite antigen standard solutions at different concentrations (1000 ppm, 500 ppm, 100 ppm, 50 ppm, 10 ppm, 5 ppm and 1 ppm) is dropped on the SERS chip, and subjected to the SERS determination. Thus, referring to FIGS. 2A to 2H and 3A to 3H, Raman spectrums are made and used as benchmarks. FIGS. 2A to 2H show Raman shift of the standard solutions of dust mite antigen Der f1. FIGS. 3A to 3H show Raman shift of the standard solution of dust mite antigen Der p1. Referring to FIG. 4 (or 5), it is learned from calculation that there is a linear relationship between the concentration of the standard solution of dust mite antigen Der f1 (or p1) and the strength of the Raman signal. That is, the strength of the Raman signal of the dust mite antigen reflects its concentration.

Figure 6:
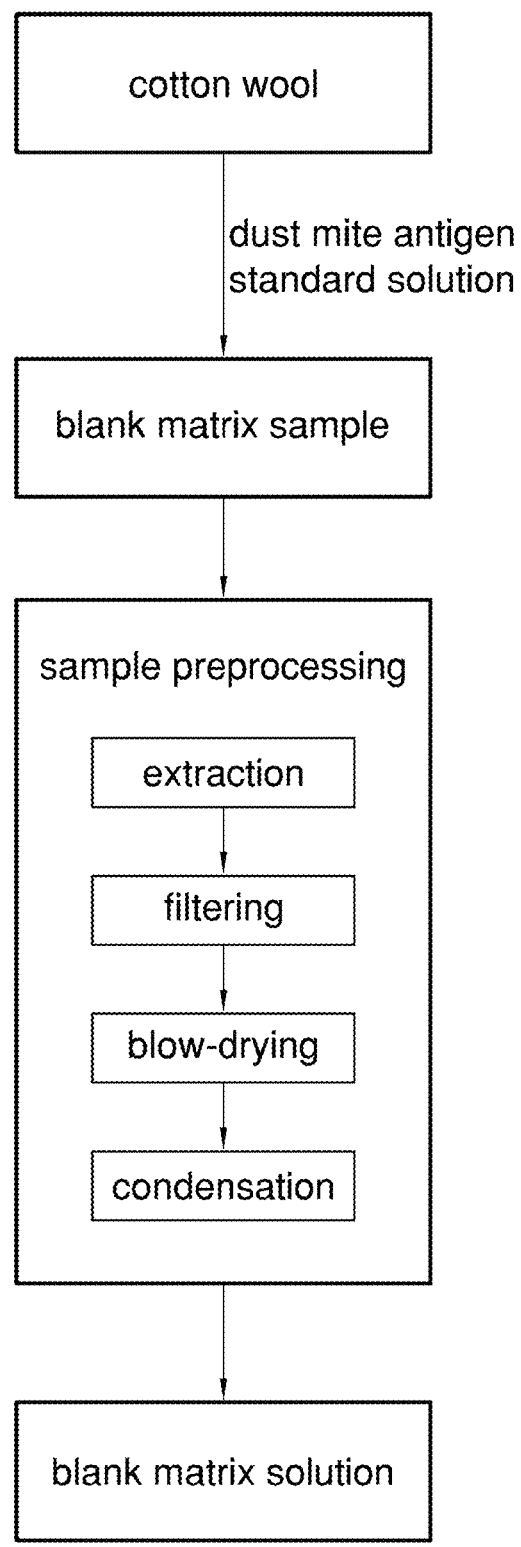
FIG. 6 is a flow chart of a procedure for producing the blank matrix sample solution.
Figure 7A:
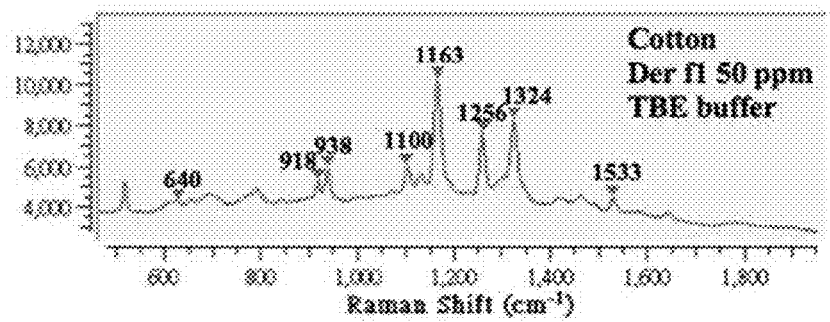
FIGS. 7A to 7D are spectrums of dust mite antigen Der f1 extracted from a dust-simulating matrix (cotton wool) in dust mite antigen Der f1 standard solutions at different concentrations in TBE extract buffer.
Figure 7B:
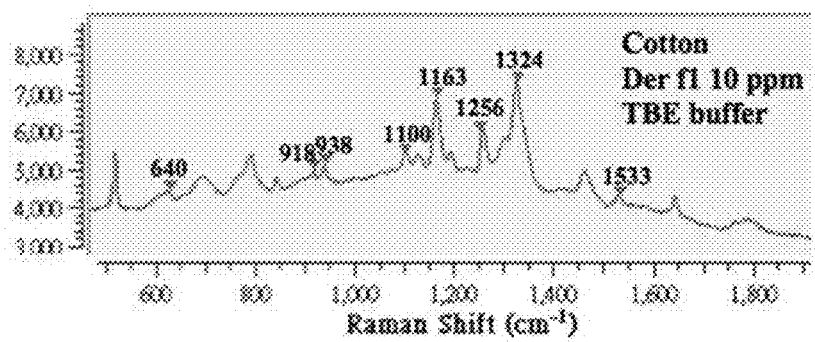
Figure 7C:
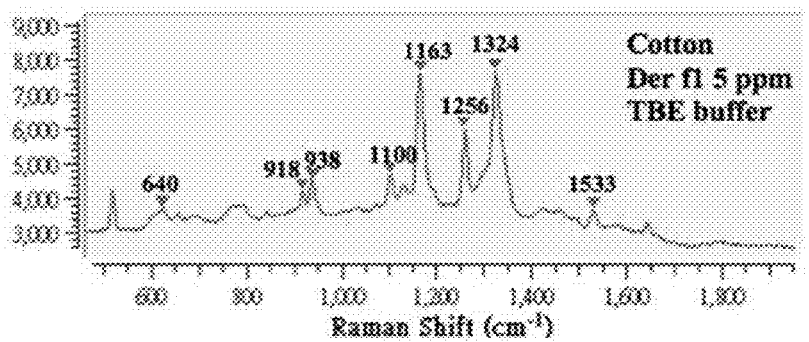
Figure 7D:
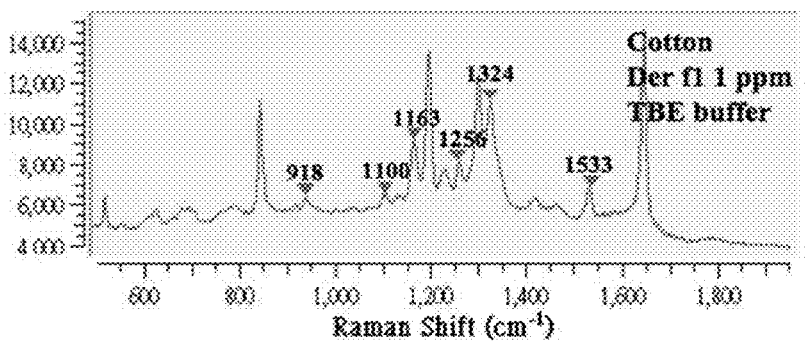
Figure 8A:
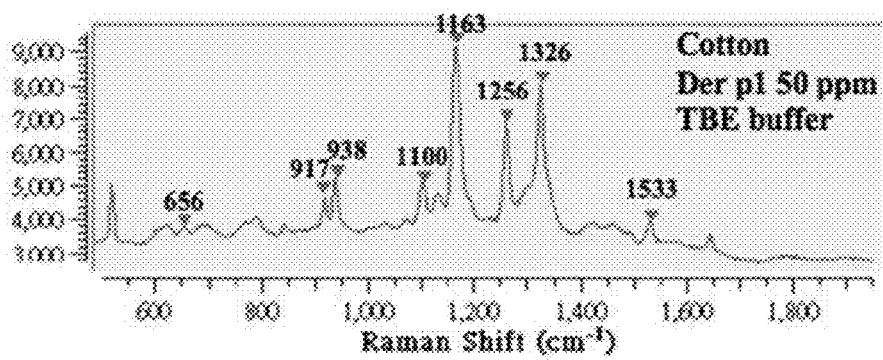
FIGS. 8A to 8D s are spectrums of dust mite antigen Der p1 extracted from a dust-simulating matrix (cotton wool) in dust mite antigen Der p1 standard solutions at different concentrations in TBE extract buffer.
Figure 8B:
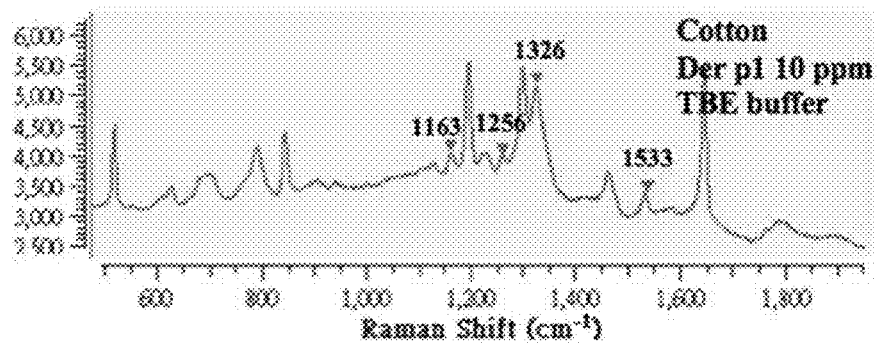
Figure 8C:
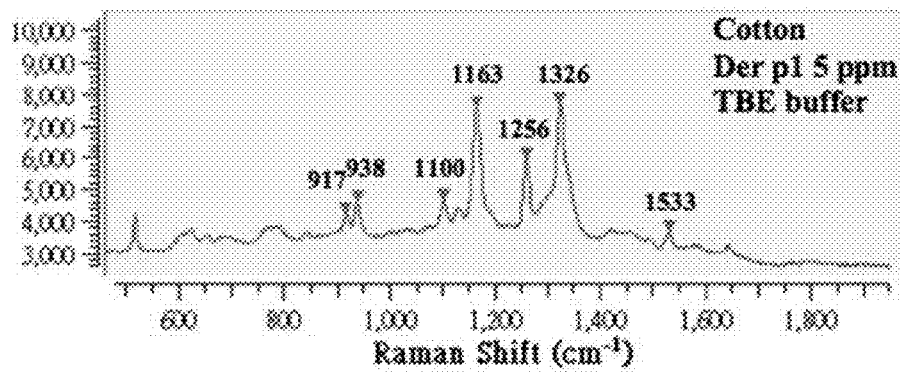
Figure 8D:
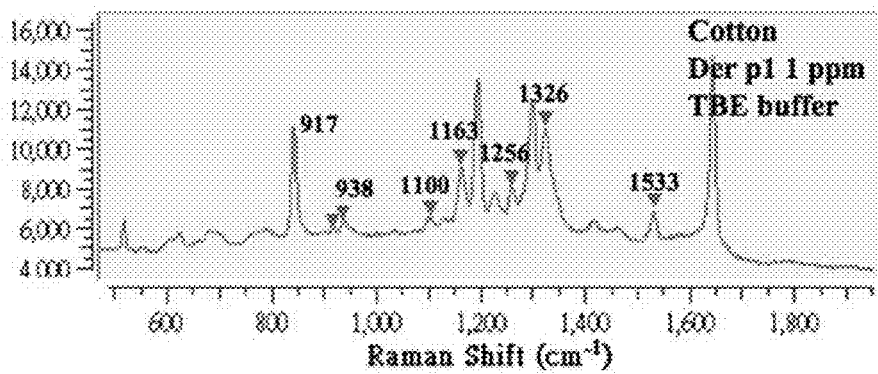

Secondly, blank-matrix sample solutions are produced. In the preferred embodiment, cotton wool is used as blank matrix to simulate an indoor dust sample referred to actual dust samples. Referring to FIG. 6, to produce the blank matrix samples, 0.01 gram of cotton wool is inserted in a glass bottle with a lining of 4 ml of brown polytetrafluoroethylene, and added with 1 µl of each of the standard solutions of dust mite antigen at different concentrations as internal labels, i.e., the blank matrix samples. The blank matrix samples are further subjected to preprocessing, and turned into blank matrix sample solutions to be used in the SERS determination. The processing of the blank matrix samples includes extraction, filtering, cleanup, blow-drying and condensation.

In the preprocessing, at first, each of the blank matrix samples is added with 500 µl of extract, and subjected to ultrasonic vibration for thorough extraction. Preferably, the extract is TBE extract buffer that includes deionized water, tris borate buffer (pH 8.5), bicarbonate (pH 8.0), phosphate (pH 7.4) and NaCl. After the extraction, a syringe with an aperture of 0.22 µm in diameter is used to filter out impurities. Then, cleanup columns are used to clean up the filtrate. The cleanup columns are filled with absorbents such as 1° or 2° amine (PSA), graphitized carbon black (GCB) and carbon-18 (C18) to effectively remove irrelevant substances and thoroughly clean up the solutions after the extraction. After the cleanup, nitrogen at a flow rate of 0.5 L/min is used to blow-dry the cleaned solution for about 5 minutes. After the blow-drying is completed, 10 µl of dust mite antigen buffer solution is added. Then, the solutions are subjected to centrifugal concentration, and laid still for about 1 minute, thereby providing condensed blank matrix sample solutions.

After the production of the blank matrix sample solution is completed, 3 µl of dust mite antigen buffer solution is dropped on the SERS chip, and subjected to SERS determination, used as a background value. Then, 3 µl of blank matrix sample solution is dropped on the SERS chip, and subjected to SERS determination.

FIGS. 7A to 7D are Raman spectrums of dust mite antigen Der f1 extracted from dust-simulating matrix (cotton wool) added with 1 µl of the standard solutions of dust mite antigen Der f1 at different concentrations (50 ppm, 10 ppm, 5 ppm and 1 ppm) and TBE extract buffer. FIGS. 8A to 8D are Raman spectrums of dust mite antigen Der p1 extracted from dust-simulating matrix (cotton wool) added with 1 µl of dust mite antigen Der p1 at different concentrations (50 ppm, 10 ppm, 5 ppm and 1 ppm) and TBE extract buffer. As shown, dust mite antigens can be detected even if the concentration of the standard solution of dust mite antigen is as low as 1 ppm, and this facilitates the monitoring of dust mites for asthma prevention.

Figure 9A:
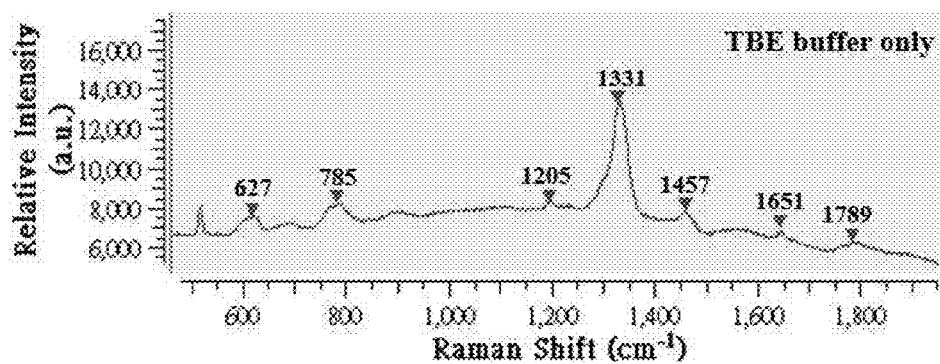
FIG. 9A is a Raman spectrum of TBE extract buffer only.
Figure 9B:
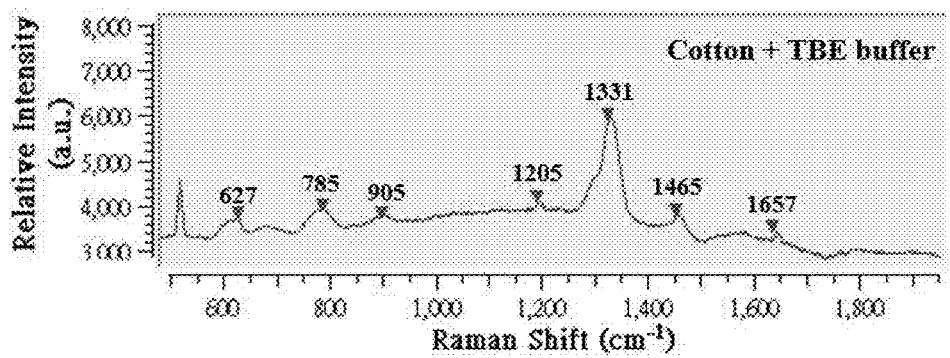
FIG. 9B is a Raman spectrum of the dust-simulating matrix processed by the TBE extract buffer.
Figure 9C:
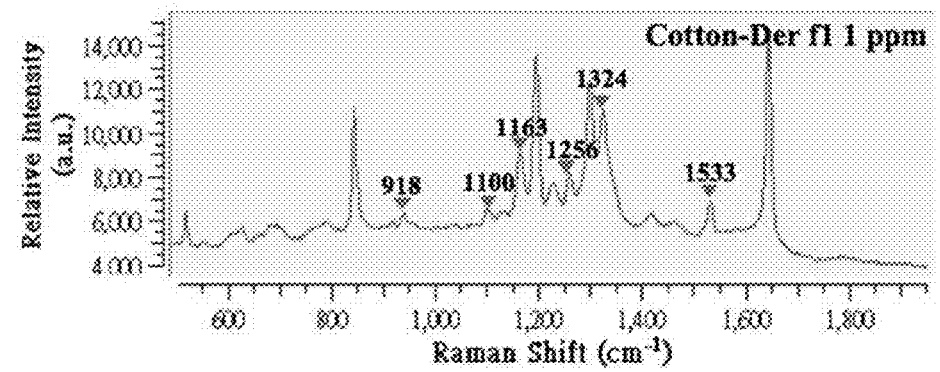
FIG. 9C is a Raman spectrum of the dust-simulating matrix added with the standard solution of dust mite antigen Der f1, and processed by the TBE extract buffer.
Figure 9D:
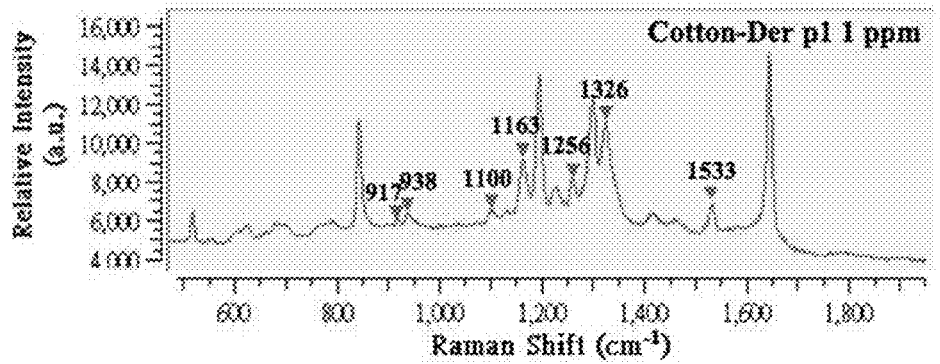
FIG. 9D is a Raman spectrum of the dust-simulating matrix added with the standard solution of dust mite antigen Der p1, and processed by the TBE extract buffer.

FIG. 9A is a Raman spectrum of only TBE extract buffer, and this Raman spectrum is used as a background value. FIG. 9B is a Raman spectrum of cotton wool added with TBE extract buffer without any internal label of dust mite antigen, and this Raman spectrum is used as a reference value. FIG. 9C is a Raman spectrum of blank matrix sample solution added with 1 µl of the standard solution of dust mite antigen Der f1 (internal label) and TBE. FIG. 9D is a Raman spectrum of blank matrix sample solution added with 1 µl of the standard solution of dust mite antigen Der f1 and TBE extract buffer. As shown, the TBE buffered extract does not affect the detection of the dust mite antigens in the dust-simulating matrix detection, and TBE extract buffer allows clear measurement of Raman signals of dust mite antigen Der f1 or dust mite antigen Der p1.

Thirdly, actual dust sample solution is produced.

Figure 10:
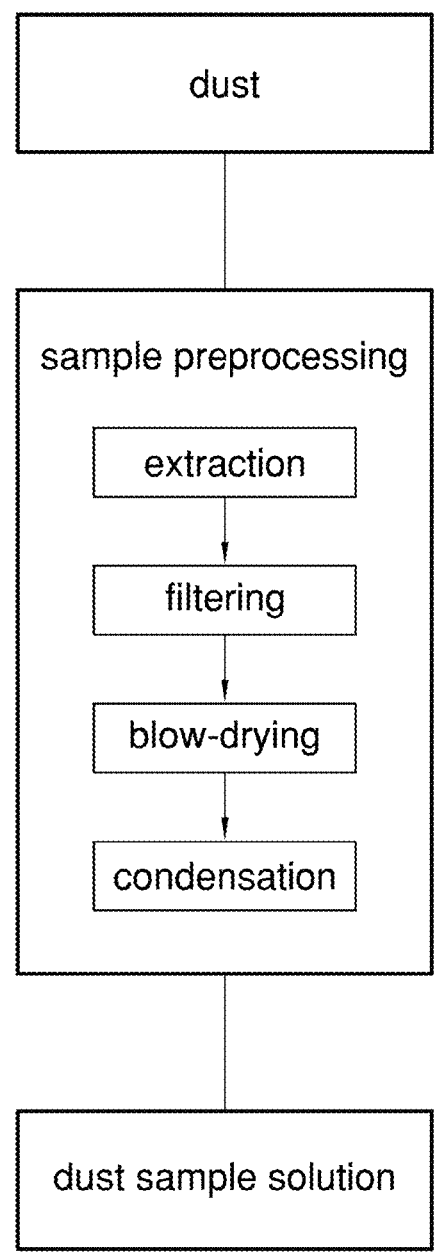
FIG. 10 is a flow chart of a process for producing actual dust sample solution according to the preferred embodiment of the present invention.

Except for the blank matrix samples, actual dust is sampled, and the actual dust is used as matrix. Referring to FIG. 10, 0.01 gram of dust is sampled, and filled in a glass bottle with a lining of 4 ml of brown polytetrafluoroethylene. The actual dust is further subjected to preprocessing to provide dust sample solution to be subjected to SERS detection. The preprocessing of the dust samples is substantially identical to the preprocessing of the blank matrix samples, and includes extraction, filtering, cleanup, blow-drying, and condensation. The preprocessing of the dust samples will be described as follows.

The dust samples are added with 500 μl of TBE extract buffer, and subjected to ultrasonic vibration for thorough extraction. The TBE extract buffer includes deionized water, Tris borate buffer (pH 8.5), bicarbonate (pH 8.0), phosphate (pH 7.4) and NaCl. After the extraction, a syringe with an aperture of 0.22 μm in diameter is used for filtering out impurities. Then, cleanup columns are used to clean up the filtered solution. The cleanup columns are filled with absorbents such as 1° or 2° amine (PSA), graphitized carbon black (GCB) and carbon-18 (C18) to effectively remove irrelevant substances and completely clean up the solutions after the extraction. After the cleanup, nitrogen at a flow rate of 0.5 L/min is used to blow-dry the cleaned solution for about 5 minutes. After the blow-drying is completed, 10 μl of dust mite antigen buffer solution is added and subjected to centrifugal concentration, and then laid still for about 1 minute, thereby providing blank matrix sample solutions.

After the production of the dust sample solutions is completed, 3 μl of dust mite antigen buffer solution is dropped on the SERS chip, subjected to SERS detection, used as a background value. Then, 3 μl of dust sample solution is dropped on the SERS chip, subjected to multiple rounds of SERS detection, and changes in Raman peaks are observed.

Figure 11A:
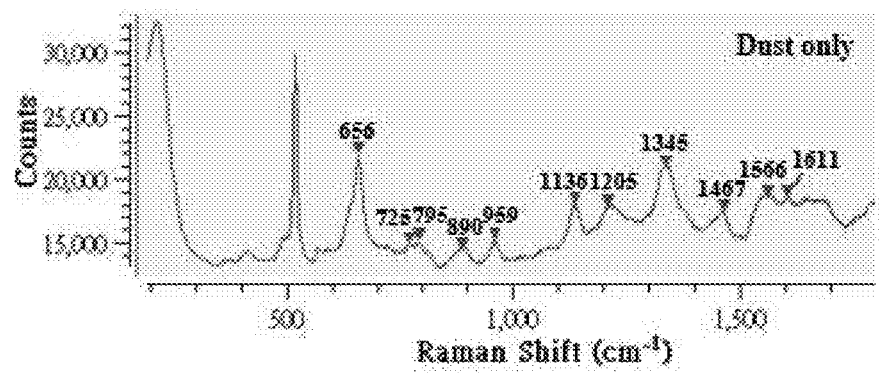
FIG. 11A is a Raman spectrum of the actual dust sample processed by the TBE extract buffer.
Figure 11B:
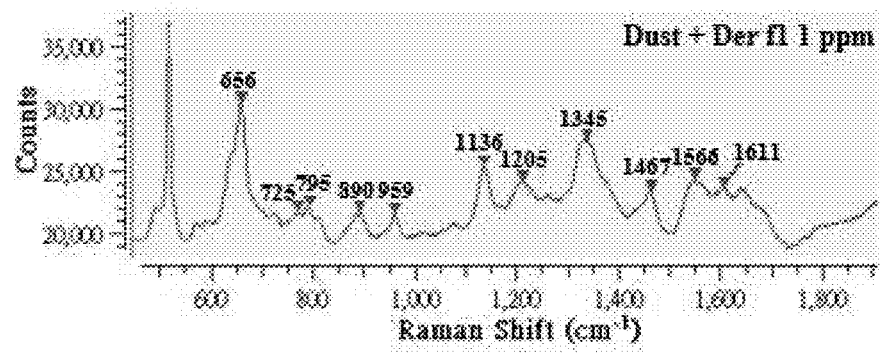
FIG. 11B is a Raman spectrum of the actual dust sample added with a dust mite antigen Der f1 internal label, and processed by the TBE extract buffer.
Figure 11C:
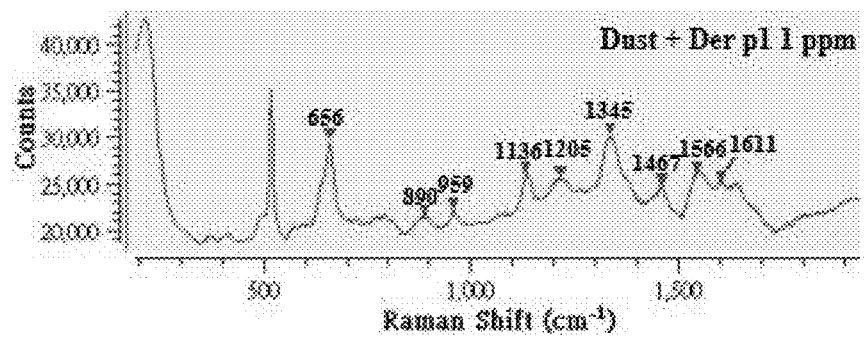
FIG. 11C is a Raman spectrum of the actual dust sample added with a dust mite antigen Der p1 internal label, and processed by the TBE extract buffer.

FIG. 11A is a Raman spectrum of the dust sample solution added with the TBE. FIG. 11B is a Raman spectrum of the dust sample solution added with an internal label of 1 μl of dust mite antigen Der f1 standard solution (1 ppm), and extracted with the TBE extract buffer. FIG. 11C is a Raman spectrum of the dust sample solution added with an internal label of 1 μl of the standard solution of dust mite antigen Der p1 (1 ppm), and extracted with the TBE extract buffer. As shown, in the sampling of the actual dust, the Raman signals of dust mite antigen Der f1 or dust mite antigen Der p1 can clearly be detected, and the Raman signals of the dust mite in the dust are in compliance with the Raman signals of the internal label of dust mite antigen Der f1 or the Raman signals of the internal label of dust mite antigen Der p1.

The present invention has been described via the illustration of the preferred embodiment. Those skilled in the art can derive variations from the preferred embodiment without departing from the scope of the present invention. Therefore, the preferred embodiment shall not limit the scope of the present invention defined in the claims.

The invention claimed is:
1. A system for detecting dust mite antigen comprising:
a SERS chip without immunological modification and used to carry a dust sample, wherein the SERS chip comprises nanogold coated on silver columns extending from a surface; and
a Raman spectrometer for imposing a surface-enhanced Raman examination on the dust sample on the SERS chip, wherein the Raman spectrometer comprises a spectrum database having information of at least one standard dust mite antigen, the information includes Raman spectrums and corresponding standard curves for a relationship between characteristic peak signals and concentrations, wherein in a Raman determination, the Raman spectrum of a to-be-examined sample is referred with the Raman spectrum of the standard dust mite antigen to determine whether any dust mite antigen identical to the standard dust mite antigen exists in the to-be-examined sample, and the standard curve is used to calculate the concentration of the dust mite antigens in the to-be-examined sample if there is dust mite antigens determined identically to the standard dust mite antigen in the to-be-examined sample.

2. The system for detecting dust mite antigen according to claim 1, wherein the standard dust mite antigen comprises a standard dust mite allergen Der p1.

3. The system for detecting dust mite antigen according to claim 1, wherein the standard dust mite antigen comprises a standard dust mite allergen Der f1.

* * * * *